(12) United States Patent
Hung et al.

(10) Patent No.: US 7,985,856 B2
(45) Date of Patent: Jul. 26, 2011

(54) METHOD FOR PREPARING HEXOSE DERIVATIVES

(75) Inventors: Shang-Cheng Hung, Taipei (TW); Cheng-Chung Wang, Taichung (TW); Jinq Chyi Lee, Hsinchu (TW); Shun Yuan Luo, Taichung (TW); Suvarn Subhash Kulkarni, Mumbai (IN); Yu Wen Huang, Rochester, NY (US); Chia Chen Lee, Rochester, NY (US); Ken Lien Chang, Taipei (TW)

(73) Assignee: National Tsing Hua University, Hsinchu (TW)

( * ) Notice: Subject to any disclaimer, the term of this patent is extended or adjusted under 35 U.S.C. 154(b) by 760 days.

(21) Appl. No.: 11/874,697

(22) Filed: Oct. 18, 2007

(65) Prior Publication Data

US 2009/0105466 A1 Apr. 23, 2009

(51) Int. Cl.
*C07H 1/00* (2006.01)
*C07G 3/00* (2006.01)
*C07H 15/04* (2006.01)
(52) U.S. Cl. ................... 536/124; 536/4.1; 536/120
(58) Field of Classification Search ............ 536/4.1, 536/120, 124
See application file for complete search history.

(56) References Cited

U.S. PATENT DOCUMENTS

| | | | | |
|---|---|---|---|---|
| 3,829,413 A | * | 8/1974 | Deslongchamps | 536/18.2 |
| 3,856,843 A | * | 12/1974 | Nagai et al. | 556/463 |
| 5,344,924 A | * | 9/1994 | Arora | 536/124 |

OTHER PUBLICATIONS

Liptak et al (Trimethylsilyl Triflate—Catalysed Acetal Formation Between Silylated Hexopyranosides and Methyl Pyruvate, J. Carbohydrate Chemistry, 8(4), 629-644 (1989).*
Document cited in Taiwanese search report dated Aug. 3, 2010 of the Taiwanese counterpart application.

* cited by examiner

*Primary Examiner* — Shaojia Anna Jiang
*Assistant Examiner* — Everett White
(74) *Attorney, Agent, or Firm* — WPAT, P.C.; Anthony King (57) ABSTRACT

A method for preparing hexose derivatives comprises the steps of providing a silylated hexose, treating the silylated hexose with a first carbonyl compound in the presence of a catalyst to form an ketalized hexose, treating the ketalized hexose with a second carbonyl compound followed by treating with a first reductant to form an etherized hexose, and converting the etherized hexose into a target hexose derivative, which can be 2-alcohol hexose, 3-alcohol hexose, 4-alcohol hexose, or a 6-alcohol hexose. In particular, the present invention can prepare the hexose derivatives with highly regioselective scheme to protect individual hydroxyls of monosaccharide units and install an orthogonal protecting group pattern in a one-pot manner.

25 Claims, 9 Drawing Sheets

I. Combinatorial, Regioselective, Orthogonal, and One-pot Protection of Hydroxyls 11
X = α- or β -OR,
α- or β -SR,
α- or β -SeR,
α- or β -F 12
fully protected monosaccharides 13
2- or 3- or 4- or 6-alcohols II. One-pot Coupling to the Synthesis of Oligosaccharides and Glycoconjugates

FIG. 3

| | |
|---|---|
| R = R$^1$ = R$^2$ = H | (Pd/C, H$_2$ or Na, NH$_3$) |
| R = Ph, R$^1$ = R$^2$ = H | (FeCl$_3$) |
| R = CN, R$^1$ = R$^2$ = H | (electrolytic reduction) |
| R = N$_3$, R$^1$ = R$^2$ = H | (PPh$_3$, H$_2$O ; DDQ) |
| R = NHPiv, R$^1$ = R$^2$ = H | (DDQ) |
| R = OMe, R$^1$ = R$^2$ = H | (DDQ or TFA) |
| R = OAc, R$^1$ = R$^2$ = H | (NaOMe) |
| R = X, R$^1$ = R$^2$ = H | (PdL$_n$, 2° amine; acid) |
| R = R$^2$ = H, R$^1$ = NO$_2$ | (photolysis) |
| R = R$^1$ = OMe, R$^2$ = H | (CeCl$_3$/7H$_2$O, NaI) |
| R = N$_3$, R$^1$ = H, R$^2$ = Cl | (TFA) |
| R, R$^2$ = ⟨fused ring⟩, R$^1$ = H | (DDQ) |

I. Influenza Virus-Binding Trisaccharide of Human Host Cell Surface SAα2,6Galβ1,4G

METHOD FOR PREPARING HEXOSE DERIVATIVES

BACKGROUND OF THE INVENTION (A) Field of the Invention

The present invention relates to a method for preparing hexose derivatives, and more particularly, to a method for preparing hexose derivatives with highly regioselective scheme to protect individual hydroxyls of monosaccharide units and install an orthogonal protecting group pattern in a one-pot manner.

(B) Description of the Related Art

Carbohydrates are involved in numerous vital life processes. They are structurally diverse and complex as compared to other biopolymers (proteins and nucleic acids) and are present in micro-heterogeneous forms in nature. Chemical synthesis of carbohydrates, the practical route to procure pure oligosaccharides, is however hampered by two major hurdles, regioselective protection of polyhydroxyls and rapid assembly of glycosidic linkages involving the stereoselective control of α- or β-glycosidic bonds.

Oligosaccharides and glycoconjugates play significant roles in a diverse set of biological processes, including viral and bacterial infections, cell growth and proliferation, cell-cell communication, as well as immuno-response. Their structural diversity, which allows them to encode information required for specific molecular recognition, and determine the posttranscriptional modification of proteins, is much more complex than that of proteins and nucleic acids. As most of the structural information of carbohydrate-protein, carbohydrate-nucleotide, and carbohydrate-carbohydrate complex at molecular level remains obscure, homogeneous materials with well-defined configurations are essential for the determination of biological function and structure-activity relationship (SAR). However, these oligosaccharides being present in micro-heterogeneous forms cannot be procured easily from natural sources in acceptable purity and amounts. Chemical methods to synthesize these function-oriented domains have therefore acquired immense importance.

In comparison with other biopolymers, peptides/proteins and nucleotides/DNA and RNA, the preparation of oligosaccharides is obviously more difficult since no regio- and stereochemical issues are involved in the sequential coupling steps for the construction of amide or phosphate bonds, respectively. The biggest challenge in carbohydrate synthesis is not only the rapid assembly of oligosaccharides involving the stereoselective control of α- or β-glycosidic bonds, but also the preparation of selectively protected monosaccharide units, one with a strategically positioned free hydroxy group (a nucleophilic acceptor) and one bearing a labile leaving group at the anomeric carbon that acts as a glycosyl donor in the ensuing glycosylation reaction. Along with this, the installation of suitable protecting groups on the remaining hydroxyls, for tuning the overall electronic properties of donors and acceptors so as to "match" the donor-acceptor pair and also for further deprotection and glycosylation or functional group modifications, is required.

Figure 1:
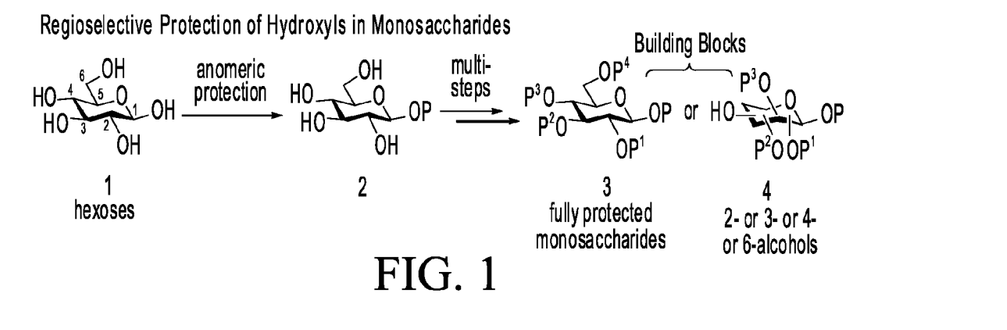
FIG. 1 illustrates a traditional chemical approach for the protection of carbohydrate.

FIG. 1 illustrates a traditional chemical approach for carbohydrate synthesis involving protection and glycosylation. A hexose 1 is well-known to be protected easily at the anomeric carbon (C1) to furnish the corresponding hexopyranoside 2 via the formation of cyclic acetal. Transformation of hexopyranoside 2 into either the fully protected monosaccharide 3 or the individual alcohols 4 with a free hydroxyl at C2, C3, C4, or C6 frequently encounters several difficulties, such as (1) an independent and multi-step protection-deprotection sequence is needed to prepare each compound (4-6 steps), (2) a tedious workup is often used in each synthetic step, (3) a time-consuming purification is required to separate different regioisomers, and (4) low yield of the expected product is sometimes obtained due to the poor regioselectivity.

Figure 2A:
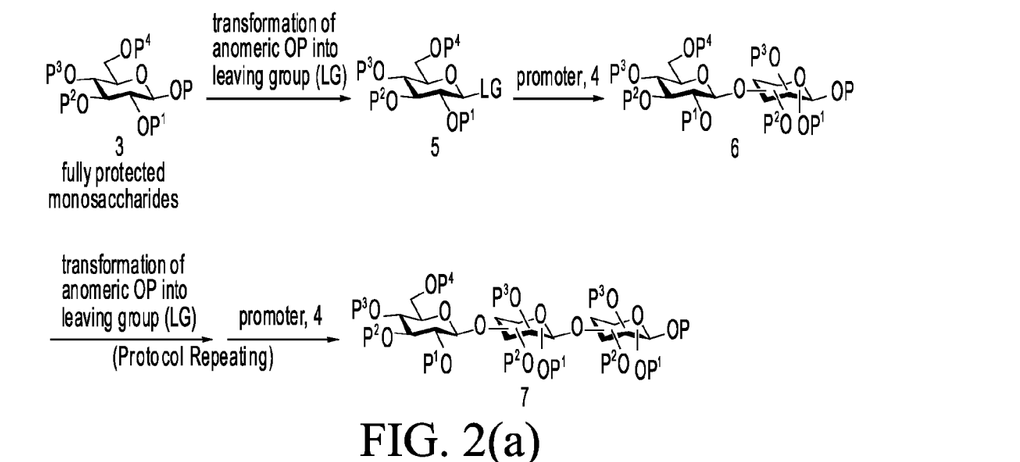
FIG. 2(a) and FIG. 2(b) illustrate traditional chemical approaches for synthesizing the target oligosaccharides from the building blocks.
Figure 2B:
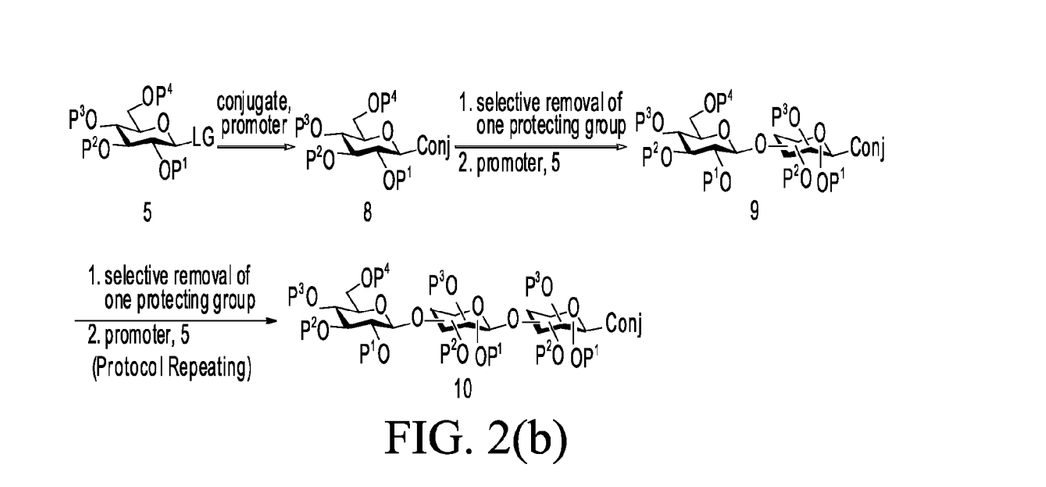

FIG. 2(a) and FIG. 2(b) illustrate traditional chemical approaches for synthesizing the target oligosaccharides from the building blocks. Once the basic building blocks are constructed, the target oligosaccharide can be stereoselectively assembled either from the non-reducing end (FIG. 2(a)) or from the reducing end (FIG. 2(b)) of the starting sugar unit. Referring to FIG. 2A, the anomeric protecting group of a fully protected monosaccharide 3 has to be converted into a labile leaving group (LG) to yield the glycosyl donor 5. This leaving group is then chemo-selectively activated using a promoter system to liberate the anomeric function and the so-formed reactive sugar intermediate is concomitantly coupled with the glycosyl acceptor 4 to give the disaccharide 6. A stepwise iteration of this protocol leads to the trisaccharide 7 and the process can be repeated to provide the higher oligosaccharides. In the alternative protocol (FIG. 2(b)), the anomeric center of compound 5 is first blocked by a conjugate group, depending on the purpose of target molecule, to obtain the reducing end saccharide 8.

The subsequent step demands selective removal of one of the protecting groups to generate the corresponding alcohol that is similarly employed in the coupling step with 15, aided by the promoter, to get the disaccharide 9. Repetition of this deprotection-glycosylation sequence provides the trisaccharide 10 and higher oligomers.

SUMMARY OF THE INVENTION

One aspect of the present invention provides a method for preparing hexose derivatives with highly regioselective scheme to protect individual hydroxyls of monosaccharide units and install an orthogonal protecting group pattern in a one-pot manner.

A method for preparing hexose derivatives according to this aspect of the present invention comprises the steps of providing a silylated hexose, treating the silylated hexose with a first carbonyl compound in the presence of a catalyst to form an ketalized hexose, treating the ketalized hexose with a second carbonyl compound followed by treating with a first reductant to form an etherized hexose, and converting the etherized hexose into a target hexose derivative.

The present method may treat the etherized hexose with silylate-removing reagent to form a 2-alcohol hexose. Furthermore, the present method may treat the etherized hexose with an electrophile under basic conditions to form a fully protected glycoside and then treat the fully protected glycoside with an oxidant to form a 3-alcohol hexose. In addition, the present method may treat the etherized hexose with an anhydride followed by treating with an acid and a second reductant to form a 4-alcohol hexose, or treating the etherized hexose with an anhydride followed by treating with a second reductant and a lewis acid to form a 6-alcohol hexose.

According to the present application, a novel, combinatorial, and highly regioselective method to protect individual hydroxyls of monosaccharide units and install an orthogonal protecting group pattern in a one-pot manner is presented, obviating the necessity to carry out intermittent tedious workups and time-consuming purifications. Hundreds of building blocks starting from hexose such as D-glucose, the most abundant sugar in nature, have been efficiently prepared, and it is expected that the protocol is equally applicable to other sugars as well. Iterative coupling of these building blocks to the assembly of β-1,6-glucans and first one-pot synthesis of influenza virus-binding trisaccharide library using a sialyl donor as the starting sugar unit are demonstrated, respectively. Thereby, the combination of one-pot protection strategy and one-pot glycosylation may offer an efficient protocol to solve the long-standing problem in carbohydrate synthesis.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 3:
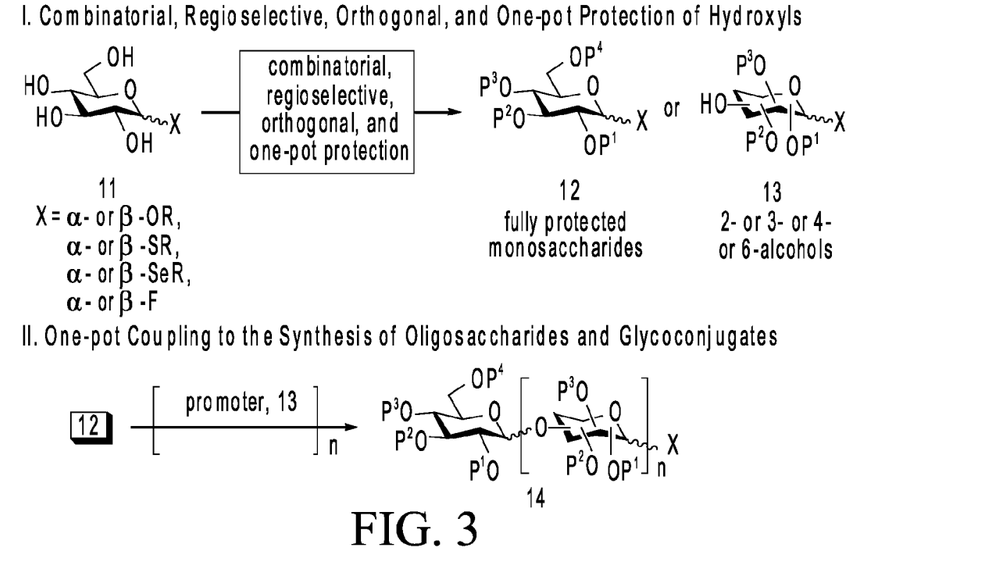
FIG. 3 illustrates a straightforward synthesis of hexose derivatives according to one embodiment of the present invention.

FIG. 3 illustrates a straightforward synthesis of glucose derivatives according to one embodiment of the present invention. It is envisioned that the 2-, 3-, 4-, and 6-hydroxy groups on a monosaccharide bearing an anomeric group (X=α- or β-OR, -SR, and -SeR) could be distinctively protected in a combinatorial, regioselective, orthogonal, and sequential one-pot procedure. Such a method would be of vital importance to expedite the overall synthetic process and reduce the labor involved in saccharide preparation.

Tetraol 11 could be selectively protected in a one-pot manner, in such a way that the hydroxy groups bear chemically differentiable protecting groups, to get either the fully protected monosaccharides 12 or the individual alcohols 13. The fully protected monosaccharides 12 or the individual alcohols 13 serving as building blocks can be rapidly coupled through one-pot glycosylation process to yield the desired oligosaccharides 14. Thus a complex oligosaccharide skeleton with various sugar units can be straightforwardly established in an efficient manner.

Figure 4:
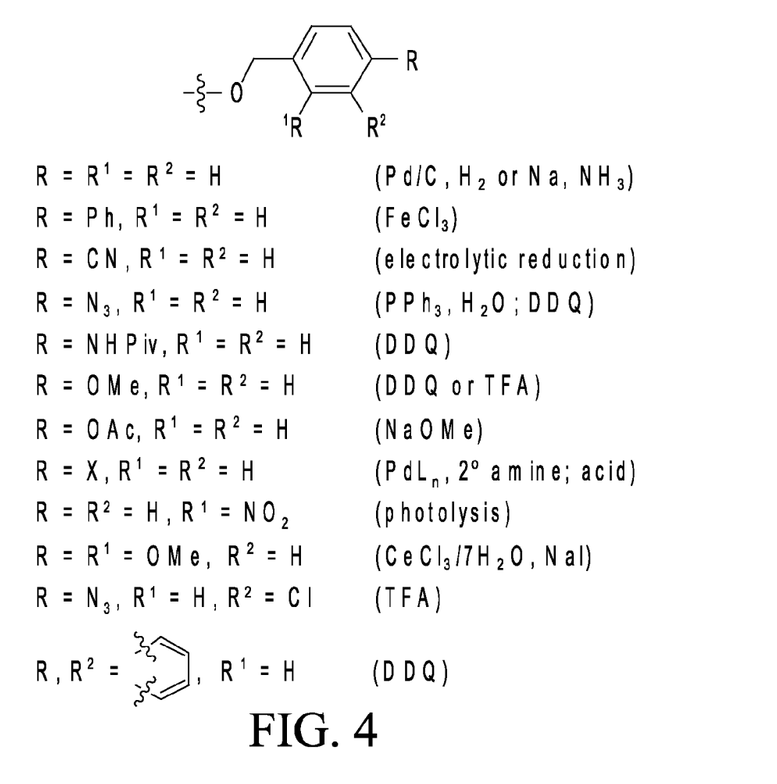
FIG. 4 illustrates the diversity of benzyl groups, and the cleavage of these substituted and unsubstituted benzyl ethers under various conditions.

FIG. 4 illustrates the diversity of benzyl groups, and the cleavage of these substituted and unsubstituted benzyl ethers under various conditions. For the successful development of combinatorial, regioselective, orthogonal and one-pot protection scheme, the choice of the protecting groups was crucial. Benzyl-type ethers, which have a larger family than esters or silyl ethers, can be selectively cleaved under appropriate conditions. As summarized in FIG. 4, benzyl group is both acid and base resistant and usually serve as permanent protecting groups that can be reduced in the final step to yield free hydroxy groups. However, substituted benzyl ethers act as orthogonal protecting groups and their cleavages are advantageously carried out by using unique reagent combination.

For example, para-methoxybenzyl (PMB) group can be cleaved by 2,3-dichlro-5,6-dicyano-1,4-benzoquinone (DDQ), ceric ammonium nitrite (CAN), or trifluoroacetic acid (TFA) whereas, 2-naphthylmethyl group (2-NAP), which is more stable than PMB in acidic condition is susceptible to only DDQ, thus be differentiated by CAN or TFA. Likewise, halogen-substituted benzyl ethers can be converted to acid-labile amino-benzyl ethers by a Pd-catalyzed reaction in the following order of reactivity I>Br>Cl>F. Strategically, the protecting group at the O2 position of a monosaccharide unit to be used as a glycosyl donor plays a pivotal role in the stereocontrol of glycosylation. Generally, benzyl-type ethers at the C2 position of the donor favor the formation of axially oriented glycosidic bonds by the virtue of the anomeric effect whereas, installation of 1,2-trans-linkage is usually achieved by the neighboring group participation of an ester type protecting group at C2. Thus, along with benzyl-type groups the incorporation of acyl groups at O2, in the one-pot protection endeavor, was pertinent.

Figure 5A:
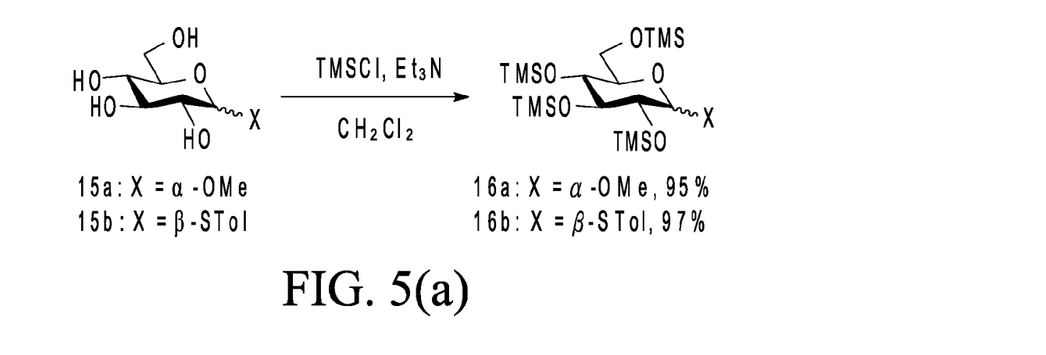
FIG. 5(a) and FIG. 5(b) illustrate the preparation of the 2,3,4,6-tetra-O-trimethylsilyl ethers according to one embodiment of the present invention.
Figure 5B:
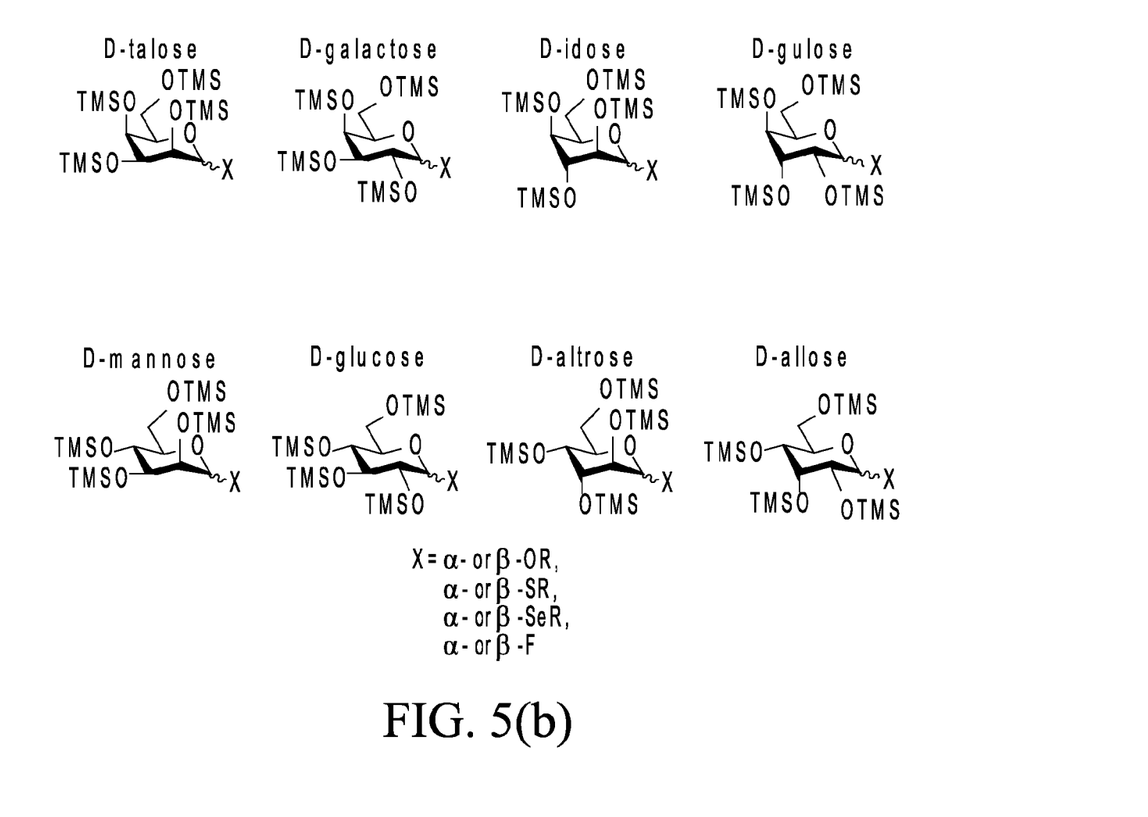

FIG. 5(a) and FIG. 5(b) illustrate the preparation of the 2,3,4,6-tetra-O-trimethylsilyl ethers according to one embodiment of the present invention. To test our strategy, D-glucose, the most abundant sugar in nature, was selected as a substrate for our studies. Methyl-D-glucopyranoside 15a and p-methylphenyl-D-thioglucopyranoside 15b were trimethylsilylated using trimethyl chlorosilane (TMSCl) and triethylamine(Et$_3$N) to afford the corresponding ethers 16a and 16b in near-quantitative yields, respectively. The per-O-silylation of sugars not only provided the requisite O-trimethylsilylated functionalities for regioselective protection, but also dramatically improved the solubility of unprotected monosaccharides in common organic solvents. In particular, D-glucose is used in the following example to describe the method for preparing the hexose derivatives, and one skilled in the art should be appreciated that the D-glucose is one of the hexose and the present invention can also be used to prepare the derivatives of hexose such as D-talose, D-galactose, D-idose, D-gulose, D-mannose, D-altrose and D-allose, as shown in FIG. 5(b).

Figure 6A:
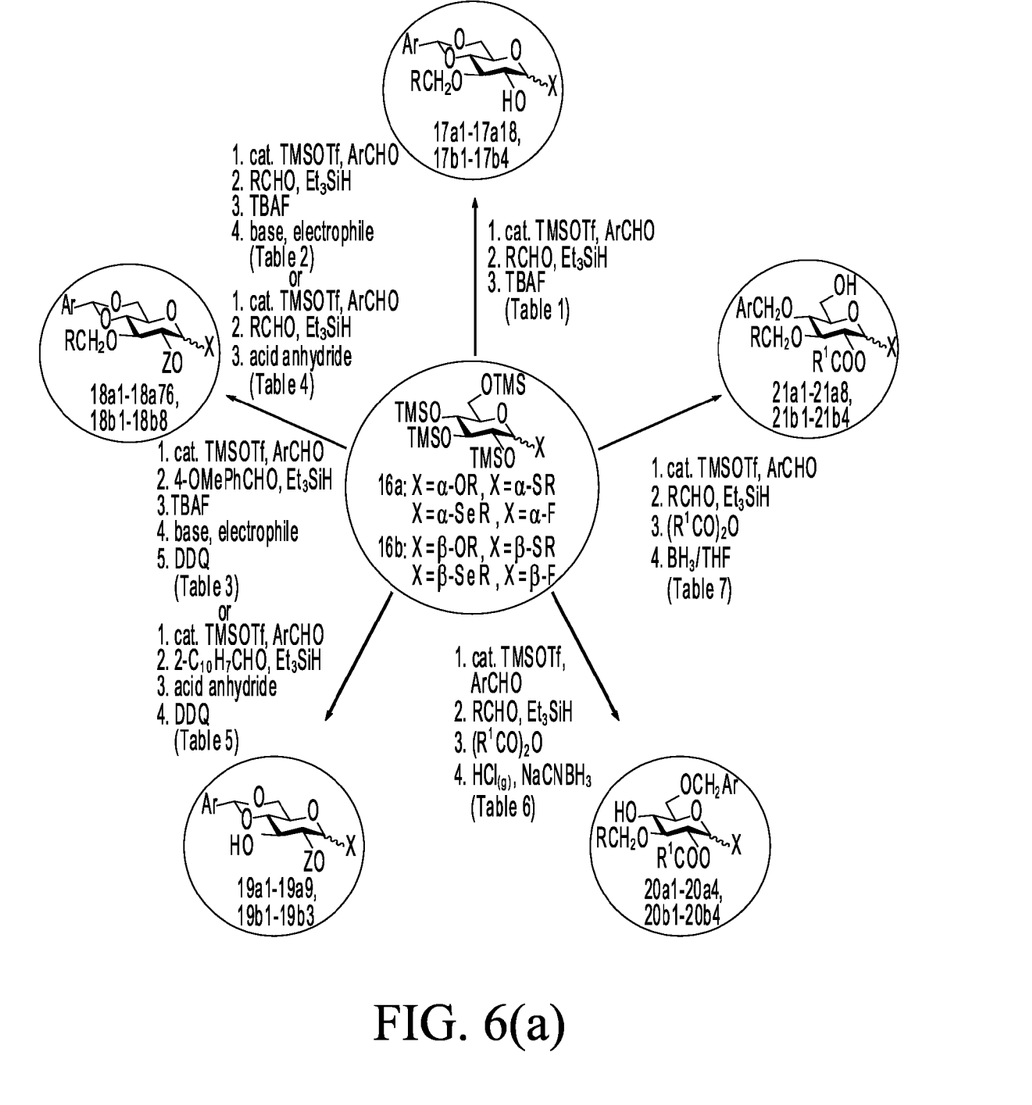
FIG. 6(a) illustrates the combinatorial, regioselective, orthogonal, and one-pot protection of 2,3,4,6-tetra-O-trimethylsilyl ethers according to one embodiment of the present invention.

FIG. 6(a) to FIG. 13 illustrate the combinatorial, regioselective, orthogonal, and one-pot protection of 2,3,4,6-tetra-O-trimethylsilyl ethers according to one embodiment of the present invention. Referring to FIG. 6(a), the general protocols involved (1) selective protection of O4 and O6 as an arylidene acetal followed by highly regioselective reductive arylmethylation at O3 to furnish the 2-alcohols, (2) O4,O6-arylidenation, O3-arylmethylation, and subsequent etherification or acylation at O2 to get the fully protected monosaccharides, (3) O4,O6-arylidenation, O3-PMB or O3-2-NAP protection, O2-etherification or O2-acylation, and removal of PMB or 2-NAP to yield the 3-alcohols, (4) O4,O6-arylidenation, O3-arylmethylation, O2-acylation, and regioselective ring opening of arylidene acetals at O4 and O6 to provide the 4-alcohols and 6-alcohols, respectively. The novelty of this approach lies in tuning of the reactions conditions in such a way so as to generate a single regioisomer at each stage that allows sequential addition of reagents in the same pot.

Figure 6B:
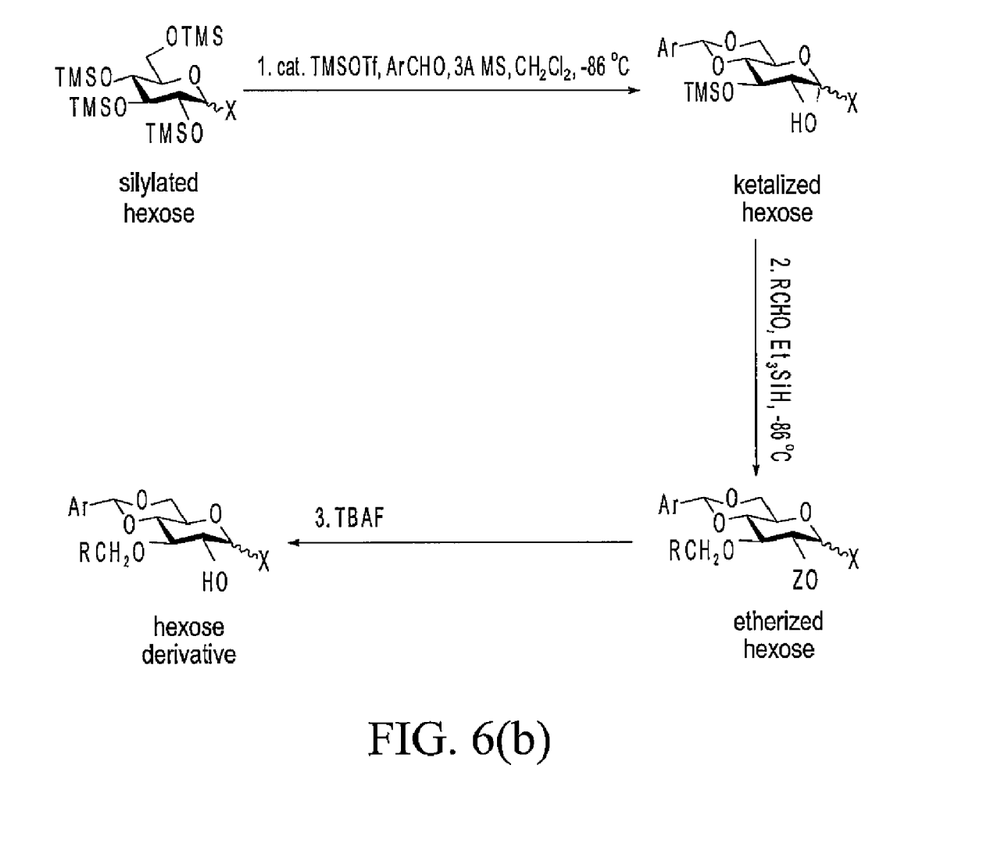
FIG. 6(b) illustrates the preparation of hexose derivatives according to one embodiment of the present invention.
Figure 7:
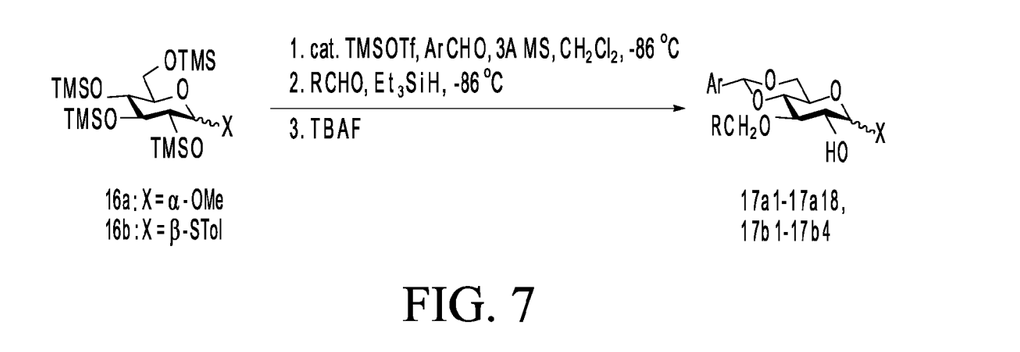
FIG. 7 illustrates the general procedure for the one-pot synthesis of 2-alcohol gluceses in Table 1 according to one embodiment of the present invention.
Figure 8:
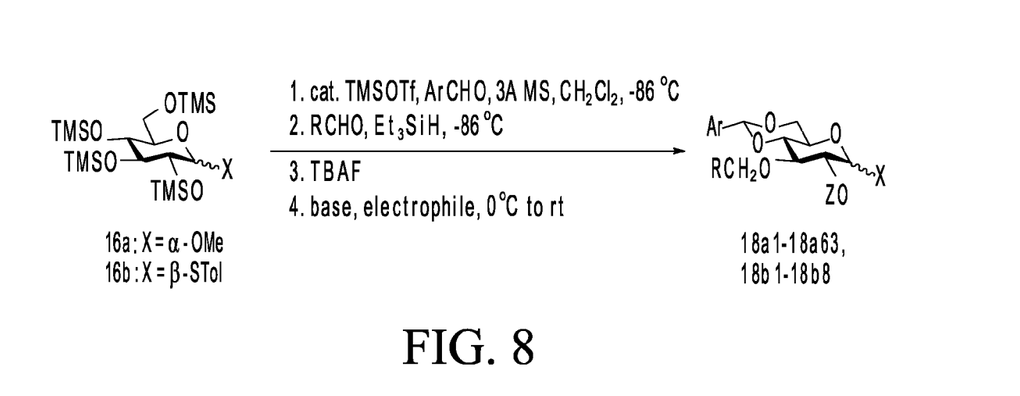
FIG. 8 illustrates the general procedure for the one-pot synthesis of fully protected monosaccharides in Table 2 according to one embodiment of the present invention.
Figure 9:
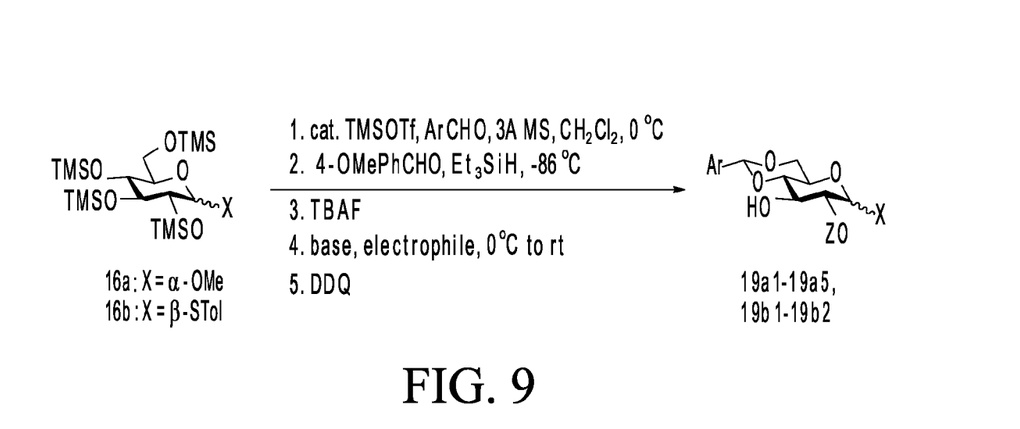
FIG. 9 illustrates the general procedure for the one-pot synthesis of 3-alcohols in Supplementary Table 3 according to one embodiment of the present invention.

Referring to FIG. 6(b), to prepare hexose derivatives according to one embodiment of the present invention, the steps may comprise providing a silylated hexose, treating the silylated hexose with a first carbonyl compound in the presence of a catalyst to form an ketalized glucose, treating the ketalized hexose with a second carbonyl compound followed by treating with a first reductant to form an etherized hexose, and converting the etherized hexose into a target hexose derivative, which can be 2-alcohol glucose, 3-alcohol glucose, 4-alcohol glucose, or a 6-alcohol glucose. The silylated glucose can be per-trimethylsilylated glucose per-triethylsilylated hexose or per-dimethylethylsilylated hexose, and the first carbonyl compound can be the same as or different from the second carbonyl compound, wherein the first carbonyl compound and the second carbonyl compound can be selected from the group consisting of aldehyde and ketone. Furthermore, the silylated hexose may include a functional group selected from the group consisting of α-OR, β-OR, α-SR, β-SR, α-SeR, β-SeR, α-F and β-F.

In addition, the catalyst can be trimethylsilyl trifluoromethanesulfonate (TMSOTf) or metal trifluoromethanesulfonate, the ketalized glucose has an arylidene acetal group, and the first reductant can be triethylsilane (Et$_3$SiH) or dimethylethyl silane to convert the carbonyl group (C=O) of the carbonyl compound (RCHO) into an ether group. The metal trifluoromethanesulfonate can be selected from the group consisting of copper(II) trifluoromethanesulfonate [Cu(OTf)$_2$], oxavanadium(IV) trifluoromethanesulfonate [V(O)(OTf)$_2$], Bismuth(III) trifluoromethanesulfonate [Bi(OTf)$_3$], Hafnium(IV) trifluoromethanesulfonate [Hf(OTf)$_4$], Samarium(III) trifluoromethanesulfonate [Sm(OTf)$_3$], Scandium(III) trifluoromethanesulfonate [Sc(OTf)$_3$], Praseodymium(III) trifluoromethanesulfonate [Pr(OTf)$_3$], Neodymium trifluoromethanesulfonate [Nd(OTf)$_3$], Ytterbium trifluoromethanesulfonate [Yb(OTf)$_3$], Europium(III) trifluoromethanesulfonate [Eu(OTf)$_3$], Gadolinium(III) trifluoromethanesulfonate [Gd(OTf)$_3$].

The present method may then treat the etherized glucose with silylate-removing reagent to form a 2-alcohol glucose, wherein the silylate-removing reagent is tetrabutylammonium fluoride (TBAF). Furthermore, the present method may treat the etherized glucose with an electrophile under basic conditions to form a fully protected glycoside and then treat the fully protected glycoside with an oxidant to form a 3-alcohol glucose when the O3 ether is PMB or 2-NAP, wherein the oxidant can be 2,3-Dichloro-5,6-dieyano-p-benzoquinone (DDQ).

The present method may treat the etherized glucose with an anhydride followed by treating with an acid and a second reductant to form a 4-alcohol glucose, wherein the acid can be hydrochloric acid (HCl) and the second reductant can be sodium cyanoborohydride (NaCNBH$_3$). Furthermore, the present method may treat the etherized glucose with an anhydride followed by treating with a second reductant and a lewis acid to form a 6-alcohol glucose, wherein the second reductant can be borane (BH$_3$) and the lewis acid can be TMSOTf. In addition, the present method may treat the etherized glucose with an anhydride to form a fully protected glycoside followed by treating the fully protected glycoside with an oxidant, which can be DDQ.

Accordingly, the starting silylated sugar 16a or 16b was first treated with 1 equivalent of aryl aldehyde in the presence of TMSOTf as a catalyst. After ring formation of arylidene acetal at O4 and O6 was completed, a different aryl aldehyde or another equivalent of the same aldehyde was added to the mixture followed by treatment with Et$_3$SiH. The reaction was exceptionally clean giving a single O3-ether; the excellent regioselectivity can be conceivably attributed to the higher nucleophilicity of the 3-oxygen atom. The mixture was then treated with TBAF to remove the TMS group at O2, and the corresponding 2-alcohols 17a1-17a18 and 17b1-17b4, as listed in Table 1, were obtained in high overall yields, respectively.

TABLE 1

One-pot synthesis of 2-alcohol glucoses

| | S.M. | Ar | R | product | yield (%) |
|---|---|---|---|---|---|
| 1 | 16a | Ph | Ph | 17a1 | 91 |
| 2 | 16a | Ph | 4-OMePh | 17a2 | 94 |
| 3 | 16a | Ph | 3,4-diOMePh | 17a3 | 81 |
| 4 | 16a | Ph | 2-naphthyl | 17a4 | 71 |
| 5 | 16a | Ph | 4-ClPh | 17a5 | 73 |
| 6 | 16a | Ph | 4-BrPh | 17a6 | 76 |
| 7 | 16a | 4-NO$_2$Ph | Ph | 17a7 | 70 |
| 8 | 16a | 4-NO$_2$Ph | 4-OMePh | 17a8 | 71 |
| 9 | 16a | 4-NO$_2$Ph | 3,4-diOMePh | 17a9 | 81 |
| 10 | 16a | 4-NO$_2$Ph | 2-naphthyl | 17a10 | 68 |
| 11 | 16a | 4-NO$_2$Ph | 4-ClPh | 17a11 | 73 |
| 12 | 16a | 4-NO$_2$Ph | 4-BrPh | 17a12 | 64 |
| 13 | 16a | 2-naphthyl | Ph | 17a13 | 80 |
| 14 | 16a | 2-naphthyl | 4-OMePh | 17a14 | 75 |
| 15 | 16a | 2-naphthyl | 2-naphthyl | 17a15 | 72 |
| 16 | 16a | 4-ClPh | Ph | 17a16 | 74 |
| 17 | 16a | 4-ClPh | 4-OMePh | 17a17 | 70 |
| 18 | 16a | 4-ClPh | 4-ClPh | 17a18 | 70 |
| 19 | 16b | Ph | Ph | 17b1 | 82 |
| 20 | 16b | Ph | 4-OMePh | 17b2 | 76 |
| 21 | 16b | Ph | 2-naphthyl | 17b3 | 72 |
| 22 | 16b | Ph | crotyl | 17b4 | 58 |

In another set of experiments, the first three steps were repeated as such, and the appropriate electrophile was added under basic conditions to get the fully protected glycosides 18a1-18a63 and 18b1-18b8 in good yields and in a one-pot manner (Table 2), including the introduction of various benzyl, allyl, and acyl type groups at the O2 position. For the preparation of 3-alcohols, PMB was used as a temporary protecting group at O3.

TABLE 2

One-pot synthesis of the fully protected glycosides

|    | S.M. | Ar         | R          | base              | electrophile           | Z                | product | yield (%) |
|----|------|------------|------------|-------------------|------------------------|------------------|---------|-----------|
| 1  | 16a  | Ph         | Ph         | Et$_3$N           | Ac$_2$O                | Ac               | 18a1    | 73        |
| 2  | 16a  | Ph         | Ph         | Et$_3$N           | BzCl                   | Bz               | 18a2    | 74        |
| 3  | 16a  | Ph         | Ph         | Et$_3$N           | ClAc$_2$O              | ClAc             | 18a3    | 75        |
| 4  | 16a  | Ph         | Ph         | NaH               | 2-C$_{11}$H$_9$Br      | 2-naphthylmethyl | 18a4    | 71        |
| 5  | 16a  | Ph         | Ph         | NaH               | 4-ClBnCl               | 4-ClBn           | 18a5    | 76        |
| 6  | 16a  | Ph         | Ph         | NaH               | 4-BrBnBr               | 4-BrBn           | 18a6    | 71        |
| 7  | 16a  | Ph         | Ph         | NaH               | AllylBr                | Allyl            | 18a7    | 74        |
| 8  | 16a  | Ph         | 4-OMePh    | Et$_3$N           | Ac$_2$O                | Ac               | 18a8    | 70        |
| 9  | 16a  | Ph         | 4-OMePh    | Et$_3$N           | BzCl                   | Bz               | 18a9    | 66        |
| 10 | 16a  | Ph         | 4-OMePh    | NaH               | BnBr                   | Bn               | 18a10   | 65        |
| 11 | 16a  | Ph         | 4-OMePh    | NaH               | 2-C$_{11}$H$_9$Br      | 2-naphthylmethyl | 18a11   | 71        |
| 12 | 16a  | Ph         | 4-OMePh    | NaH               | 4-ClBnCl               | 4-ClBn           | 18a12   | 67        |
| 13 | 16a  | Ph         | 4-OMePh    | NaH               | 4-BrBnBr               | 4-BrBn           | 18a13   | 65        |
| 14 | 16a  | Ph         | 4-OMePh    | NaH               | AllylBr                | Allyl            | 18a14   | 61        |
| 15 | 16a  | Ph         | 2-naphthyl | Et$_3$N           | Ac$_2$O                | Ac               | 18a15   | 63        |
| 16 | 16a  | Ph         | 2-naphthyl | Et$_3$N           | BzCl                   | Bz               | 18a16   | 62        |
| 17 | 16a  | Ph         | 2-naphthyl | NaH               | BnBr                   | Bn               | 18a17   | 71        |
| 18 | 16a  | Ph         | 2-naphthyl | NaH               | PMBCl                  | PMB              | 18a18   | 60        |
| 19 | 16a  | Ph         | 2-naphthyl | NaH               | 4-BrBnBr               | 4-BrBn           | 18a19   | 76        |
| 20 | 16a  | Ph         | 2-naphthyl | NaH               | AllylBr                | Allyl            | 18a20   | 71        |
| 21 | 16a  | Ph         | 4-ClPh     | Et$_3$N           | Ac$_2$O                | Ac               | 18a21   | 63        |
| 22 | 16a  | Ph         | 4-ClPh     | NaH               | BnBr                   | Bn               | 18a22   | 60        |
| 23 | 16a  | Ph         | 4-ClPh     | NaH               | 2-C$_{11}$H$_9$Br      | 2-naphthylmethyl | 18a23   | 66        |
| 24 | 16a  | Ph         | 4-ClPh     | NaH               | 4-BrBnBr               | 4-BrBn           | 18a24   | 60        |
| 25 | 16a  | Ph         | 4-ClPh     | NaH               | AllylBr                | Allyl            | 18a25   | 73        |
| 26 | 16a  | Ph         | 4-BrPh     | Et$_3$N           | Ac$_2$O                | Ac               | 18a26   | 64        |
| 27 | 16a  | Ph         | 4-BrPh     | Et$_3$N           | BzCl                   | Bz               | 18a27   | 61        |
| 28 | 16a  | Ph         | 4-BrPh     | NaH               | BnBr                   | Bn               | 18a28   | 62        |
| 29 | 16a  | Ph         | 4-BrPh     | NaH               | 2-C$_{11}$H$_9$Br      | 2-naphthylmethyl | 18a29   | 64        |
| 30 | 16a  | Ph         | 4-BrPh     | NaH               | AllylBr                | Allyl            | 18a30   | 62        |
| 31 | 16a  | 2-naphthyl | Ph         | Et$_3$N           | Ac$_2$O                | Ac               | 18a31   | 60        |
| 32 | 16a  | 2-naphthyl | Ph         | Et$_3$N           | BzCl                   | Bz               | 18a32   | 74        |
| 33 | 16a  | 2-naphthyl | Ph         | NaH               | BnBr                   | Bn               | 18a33   | 73        |
| 34 | 16a  | 2-naphthyl | Ph         | NaH               | PMBCl                  | PMB              | 18a34   | 90        |
| 35 | 16a  | 2-naphthyl | Ph         | NaH               | 2-C$_{11}$H$_9$Br      | 2-naphthylmethyl | 18a35   | 65        |
| 36 | 16a  | 2-naphthyl | Ph         | NaH               | 4-ClBnCl               | 4-ClBn           | 18a36   | 70        |
| 37 | 16a  | 2-naphthyl | Ph         | NaH               | AllylBr                | Allyl            | 18a37   | 72        |
| 38 | 16a  | 2-naphthyl | 4-OMePh    | Et$_3$N           | Ac$_2$O                | Ac               | 18a38   | 86        |
| 39 | 16a  | 2-naphthyl | 4-OMePh    | Et$_3$N           | BzCl                   | Bz               | 18a39   | 76        |
| 40 | 16a  | 2-naphthyl | 4-OMePh    | NaH               | BnBr                   | Bn               | 18a40   | 85        |
| 41 | 16a  | 2-naphthyl | 4-OMePh    | NaH               | 4-BrBnBr               | 4-BrBn           | 18a41   | 66        |
| 42 | 16a  | 2-naphthyl | 4-OMePh    | NaH               | 2-C$_{11}$H$_9$Br      | 2-naphthylmethyl | 18a42   | 67        |
| 43 | 16a  | 2-naphthyl | 4-OMePh    | NaH               | AllylBr                | Allyl            | 18a43   | 62        |
| 44 | 16a  | 2-naphthyl | 2-naphthyl | Et$_3$N           | Ac$_2$O                | Ac               | 18a44   | 71        |
| 45 | 16a  | 2-naphthyl | 2-naphthyl | Et$_3$N           | BzCl                   | Bz               | 18a45   | 72        |
| 46 | 16a  | 2-naphthyl | 2-naphthyl | NaH               | BnBr                   | Bn               | 18a46   | 71        |
| 47 | 16a  | 2-naphthyl | 2-naphthyl | NaH               | PMBCl                  | PMB              | 18a47   | 70        |
| 48 | 16a  | 2-naphthyl | 2-naphthyl | NaH               | 4-BrBnBr               | 4-BrBn           | 18a48   | 71        |
| 49 | 16a  | 2-naphthyl | 2-naphthyl | NaH               | 4-ClBnCl               | 4-ClBn           | 18a49   | 61        |
| 50 | 16a  | 2-naphthyl | 2-naphthyl | NaH               | AllylBr                | Allyl            | 18a50   | 77        |
| 51 | 16a  | 2-naphthyl | 4-ClPh     | Et$_3$N           | Ac$_2$O                | Ac               | 18a51   | 65        |
| 52 | 16a  | 2-naphthyl | 4-ClPh     | Et$_3$N           | BzCl                   | Bz               | 18a52   | 63        |
| 53 | 16a  | 2-naphthyl | 4-ClPh     | NaH               | BnBr                   | Bn               | 18a53   | 60        |
| 54 | 16a  | 2-naphthyl | 4-ClPh     | NaH               | 4-BrBnBr               | 4-BrBn           | 18a54   | 62        |
| 55 | 16a  | 2-naphthyl | 4-ClPh     | NaH               | 2-C$_{11}$H$_9$Br      | 2-naphthylmethyl | 18a55   | 61        |
| 56 | 16a  | 2-naphthyl | 4-ClPh     | NaH               | AllylBr                | Allyl            | 18a56   | 60        |
| 57 | 16a  | 2-naphthyl | 4-BrPh     | Et$_3$N           | Ac$_2$O                | Ac               | 18a57   | 65        |
| 58 | 16a  | 2-naphthyl | 4-BrPh     | Et$_3$N           | BzCl                   | Bz               | 18a58   | 62        |
| 59 | 16a  | 2-naphthyl | 4-BrPh     | NaH               | BnBr                   | Bn               | 18a59   | 63        |
| 60 | 16a  | 2-naphthyl | 4-BrPh     | NaH               | PMBCl                  | PMB              | 18a60   | 61        |
| 61 | 16a  | 2-naphthyl | 4-BrPh     | NaH               | 2-C$_{11}$H$_9$Br      | 2-naphthylmethyl | 18a61   | 70        |
| 62 | 16a  | 2-naphthyl | 4-BrPh     | NaH               | 4-ClBnCl               | 4-ClBn           | 18a62   | 70        |
| 63 | 16a  | 2-naphthyl | 4-BrPh     | NaH               | AllylBr                | Allyl            | 18a63   | 73        |
| 64 | 16b  | Ph         | Ph         | Et$_3$N           | Ac$_2$O                | Ac               | 18b1    | 75        |
| 65 | 16b  | Ph         | Ph         | Et$_3$N           | BzCl                   | Bz               | 18b2    | 82        |
| 66 | 16b  | Ph         | 4-OMePh    | Et$_3$N           | Ac$_2$O                | Ac               | 18b3    | 61        |
| 67 | 16b  | Ph         | 4-OMePh    | Et$_3$N           | BzCl                   | Bz               | 18b4    | 60        |
| 68 | 16b  | Ph         | 4-OMePh    | NaH               | BnBr                   | Bn               | 18b5    | 69        |
| 69 | 16b  | Ph         | 4-OMePh    | NaH               | AllylBr                | Allyl            | 18b6    | 71        |
| 70 | 16b  | Ph         | 2-naphthyl | Et$_3$N           | Ac$_2$O                | Ac               | 18b7    | 61        |
| 71 | 16b  | Ph         | 2-naphthyl | Et$_3$N           | BzCl                   | Bz               | 18b8    | 51        |

The same operation, as described for the fully protected glycosides, was repeated, DDQ was finally added to the reaction mixture, and the 3-OH compounds 19a1-19a5 and 19b1-b2 were obtained (Table 3).

TABLE 3

One-pot synthesis of 3-alcohols glucose

| | S.M. | Ar | base | electrophile | Z | product | yield (%) |
|---|---|---|---|---|---|---|---|
| 1 | 16a | Ph | Et$_3$N | Ac$_2$O | Ac | 19a1 | 52 |
| 2 | 16a | Ph | Et$_3$N | BzCl | Bz | 19a2 | 61 |
| 3 | 16a | Ph | NaH | BnBr | Bn | 19a3 | 60 |
| 4 | 16a | Ph | NaH | 4-BrBnBr | 4-BrBn | 19a4 | 60 |
| 5 | 16a | Ph | NaH | AllylBr | Allyl | 19a5 | 73 |
| 6 | 16b | Ph | NaH | BnBr | Bn | 19b1 | 65 |
| 7 | 16b | Ph | NaH | AllylBr | Allyl | 19b2 | 70 |

It was realized that O2-acylation of the 2-OTMS intermediate, generated after first two steps, could be achieved under the prevailing acidic conditions of TMSOTf as well, using acyl anhydride as a reagent to afford the fully protected monosaccharides (Table 4, 18a1, 18a2, 18a15, 18a16, 18a26, 18a27, 18a31, 18a32, 18a44, 18a45, 18a64-18a76 and 18b1, 18b2, 18b7, 18b8).

TABLE 4

One-pot synthesis of the fully protected glycosides

| | S.M. | Ar | R | Z | product | yield (%) |
|---|---|---|---|---|---|---|
| 1 | 16a | Ph | Ph | Ac | 18a1 | 94 |
| 2 | 16a | Ph | Ph | Bz | 18a2 | 67 |
| 3 | 16a | Ph | 2-naphthyl | Ac | 18a15 | 70 |
| 4 | 16a | Ph | 2-naphthyl | Bz | 18a16 | 67 |
| 5 | 16a | Ph | 4-ClPh | Ac | 18a21 | 88 |
| 6 | 16a | Ph | 4-ClPh | Bz | 18a64 | 62 |
| 7 | 16a | Ph | 4-BrPh | Ac | 18a26 | 71 |
| 8 | 16a | Ph | 4-BrPh | Bz | 18a27 | 55 |
| 9 | 16a | 4-NO$_2$Ph | Ph | Ac | 18a65 | 70 |
| 10 | 16a | 4-NO$_2$Ph | Ph | Bz | 18a66 | 61 |
| 11 | 16a | 4-NO$_2$Ph | 2-naphthyl | Ac | 18a67 | 68 |
| 12 | 16a | 4-NO$_2$Ph | 2-naphthyl | Bz | 18a68 | 62 |
| 13 | 16a | 4-NO$_2$Ph | 4-ClPh | Ac | 18a69 | 72 |
| 14 | 16a | 4-NO$_2$Ph | 4-ClPh | Bz | 18a70 | 57 |
| 15 | 16a | 4-NO$_2$Ph | 4-BrPh | Ac | 18a71 | 79 |
| 16 | 16a | 4-NO$_2$Ph | 4-BrPh | Bz | 18a72 | 64 |
| 17 | 16a | 2-naphthyl | Ph | Ac | 18a31 | 79 |
| 18 | 16a | 2-naphthyl | Ph | Bz | 18a32 | 63 |
| 19 | 16a | 2-naphthyl | 2-naphthyl | Ac | 18a44 | 72 |
| 20 | 16a | 2-naphthyl | 2-naphthyl | Bz | 18a45 | 57 |
| 21 | 16a | 4-ClPh | Ph | Ac | 18a73 | 86 |
| 22 | 16a | 4-ClPh | Ph | Bz | 18a74 | 75 |
| 23 | 16a | 4-ClPh | 4-ClPh | Ac | 18a75 | 91 |
| 24 | 16a | 4-ClPh | 4-ClPh | Bz | 18a76 | 73 |
| 25 | 16b | Ph | Ph | Ac | 18b1 | 78 |
| 26 | 16b | Ph | Ph | Bz | 18b2 | 71 |
| 27 | 16b | Ph | 2-naphthyl | Ac | 18b7 | 70 |
| 28 | 16b | Ph | 2-naphthyl | Bz | 18b8 | 56 |

Likewise, the 3-alcohol glucose derivatives 19a1, 19a6-19a9 and 19b3 were isolated in good yields via subsequent oxidative cleavage of the 2-NAP group at O3 with DDQ in one flask (Table 5).

TABLE 5

One-pot synthesis of 3-alcohol glucoses

| | S.M. | Ar | acid anhydride | Z | product | yield (%) |
|---|---|---|---|---|---|---|
| 1 | 16a | Ph | Ac$_2$O | Ac | 19a1 | 81 |
| 2 | 16a | 4-ClPh | Ac$_2$O | Ac | 19a6 | 79 |
| 3 | 16a | 4-ClPh | Bz$_2$O | Bz | 19a7 | 60 |
| 4 | 16a | 4-BrPh | Ac$_2$O | Ac | 19a8 | 75 |
| 5 | 16a | 4-BrPh | Bz$_2$O | Bz | 19a9 | 71 |
| 6 | 16b | Ph | Ac$_2$O | Ac | 19b3 | 61 |

The 4-alcohol glucoses (Table 6, 20a1-20a4 and 20b1-20b4) and 6-alcohol glucoses (Table 7, 21a1-21a8 and 21b1-21b4) were in turn accessed via regioselective O4- and O6-ring opening of arylidene acetals, formed by tandem transformations, O4,O6-arylidenation, O3-arylmethylation, and O2-acylation, on 16a or 16b, in the same pot using HCl$_{(g)}$/NaBH$_3$CN and BH$_3$/THF as reductants, respectively. Thus, D-glucopyranosides can be efficiently transformed into various glycosyl donors and acceptors bearing chemically differentiable protective groups.

TABLE 6

One-pot synthesis of 4-alcohol glucoses

| | S.M. | Ar | R | R$^1$ | product | yield (%) |
|---|---|---|---|---|---|---|
| 1 | 16a | Ph | Ph | CH$_3$ | 20a1 | 50 |
| 2 | 16a | Ph | Ph | Ph | 20a2 | 51 |
| 3 | 16a | 2-naphthyl | Ph | CH$_3$ | 20a3 | 51 |
| 4 | 16a | 2-naphthyl | 2-naphthyl | Ph | 20a4 | 50 |
| 5 | 16b | Ph | Ph | CH$_3$ | 20b1 | 70 |
| 6 | 16b | Ph | Ph | Ph | 20b2 | 57 |
| 7 | 16b | Ph | 2-naphthyl | CH$_3$ | 20b3 | 67 |
| 8 | 16b | Ph | 2-naphthyl | Ph | 20b4 | 53 |

TABLE 7

One-pot synthesis of 6-alcohol glucoses

| entry | S.M. | Ar | R | R$^1$ | product | yield (%) |
|---|---|---|---|---|---|---|
| 1 | 16a | Ph | Ph | CH$_3$ | 21a1 | 60 |
| 2 | 16a | Ph | Ph | Ph | 21a2 | 65 |
| 3 | 16a | Ph | 2-naphthyl | CH$_3$ | 21a3 | 60 |
| 4 | 16a | Ph | 2-naphthyl | Ph | 21a4 | 61 |
| 5 | 16a | 2-naphthyl | Ph | CH$_3$ | 21a5 | 60 |
| 6 | 16a | 2-naphthyl | Ph | Ph | 21a6 | 62 |
| 7 | 16a | 2-naphthyl | 2-naphthyl | CH$_3$ | 21a7 | 63 |
| 8 | 16a | 2-naphthyl | 2-naphthyl | Ph | 21a8 | 65 |
| 9 | 16b | Ph | Ph | CH$_3$ | 21b1 | 53 |
| 10 | 16b | Ph | Ph | Ph | 21b2 | 62 |
| 11 | 16b | Ph | 2-naphthyl | CH$_3$ | 21b3 | 61 |
| 12 | 16b | Ph | 2-naphthyl | Ph | 21b4 | 50 |

Figure 14:
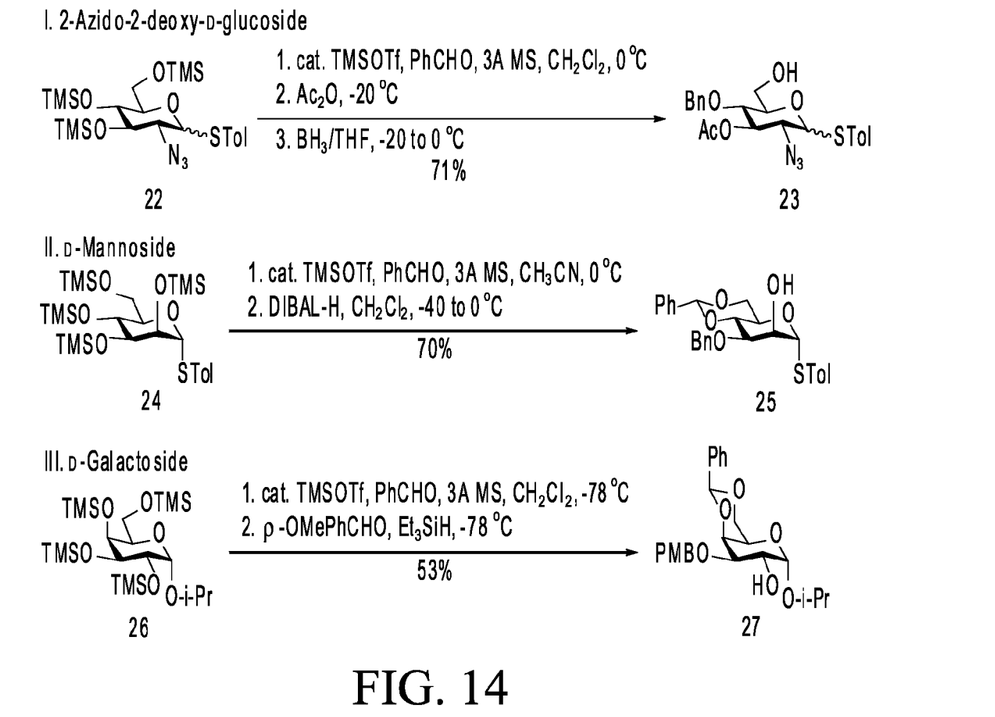
FIG. 14 illustrates one representative example for the one-pot protection of each 2-azido-2-deoxy-D-glucoside, D-mannoside, and D-galactoside according to the present invention.

FIG. 14 illustrates one representative example for the one-pot protection of each 2-azido-2-deoxy-D-glucoside, D-mannoside, and D-galactoside according to the present invention. The preliminary results indicate that this one-pot protection protocol can be adopted for other sugars as well. A representative example of each 2-azido-2-deoxy-D-glucoside, D-mannoside, and D-galactoside is illustrated. TMSOTf-catalyzed one-pot transformation of 2-azido2-deoxy-D-thioglucoside 22 via O4,O6-benzylidenation, O3-acetylation, and regioselective O6-ring opening of benzylidene acetal afforded the corresponding 6-alcohol 23 in good overall yield (I). In the case of D-mannoside, reaction of the tetra-O-TMS-D-thiomannoside 24 with two equivalents of PhCHO in the presence of TMSOTf as a catalyst led to a single 2,3:4,6-di- 
O-benzylidenated exo-isomer, which could be regioselectively opened at O2 using DIBAL-H to give the 2-alcohol 25 in 70% yield (II). The tetra-O-silylated-D-galactoside 26 could be similarly converted into the desired 2-alcohol 27 (53%) via TMSOTf-catalyzed one-pot O4,O6-benzylidenation with PhCHO followed by Et$_3$SiH-reductive etherification with p-OMePhCHO.

Figure 15:
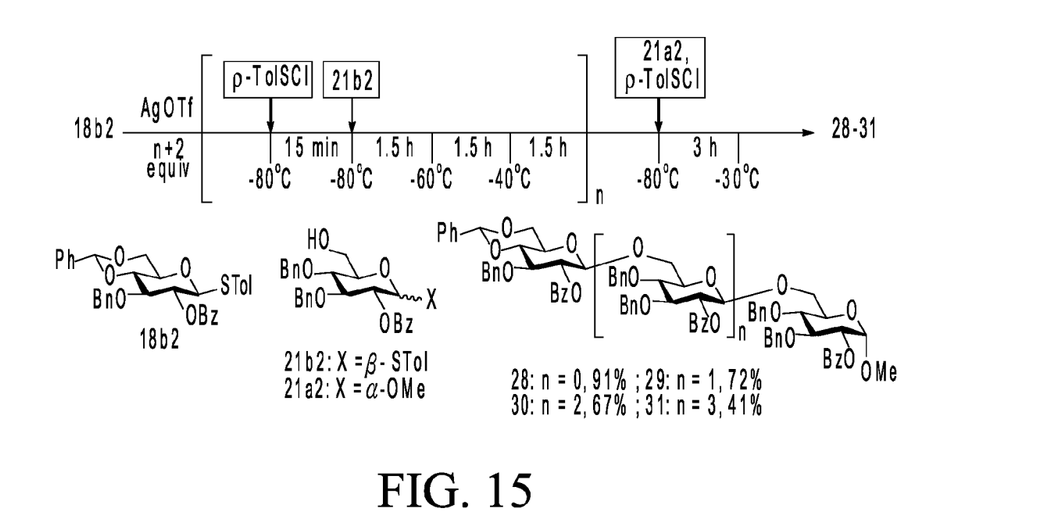
FIG. 15 illustrates the synthesis of β-1,6-glucans via iterative one-pot glycosylation according to one embodiment of the present invention.

FIG. 15 illustrates the synthesis of β-1,6-glucans via iterative one-pot glycosylation according to one embodiment of the present invention. With these diverse building blocks in hand, we further investigated the iterative one-pot glycosylation for the assembly of β-1,6-glucan oligosaccharides with various chain lengths. Monosaccharides 18b2, 21b2, and 21a2 were utilized as the starting, elongation, and termination units, respectively. Coupling of 18b2 with 21a2 promoted by p-tolunesulfenyl trifluoromethanesulfonate (p-TolSOTf, generated from AgOTf and p-TolSCl in situ), furnished the disaccharide 28 in excellent yield (91%). In another experiment, the thioglycoside 18b2 was activated first, the acceptor 21 b2 was introduced in the coupling stage (n=1), and the anomeric function of the formed disaccharide was again activated by addition of stoichiometric amount of promoter to couple with the terminating sugar unit 21a2 to afford the trisaccharide 29 (72%), efficiently. In similar way, the coupling of the elongation unit 21b2 was repeated twice (n=2) and thrice (n=3), and the tetrasaccharide 30 and pentasaccharide 31 were rapidly assembled in a one-pot manner and in good overall yields, respectively.

Figure 16:
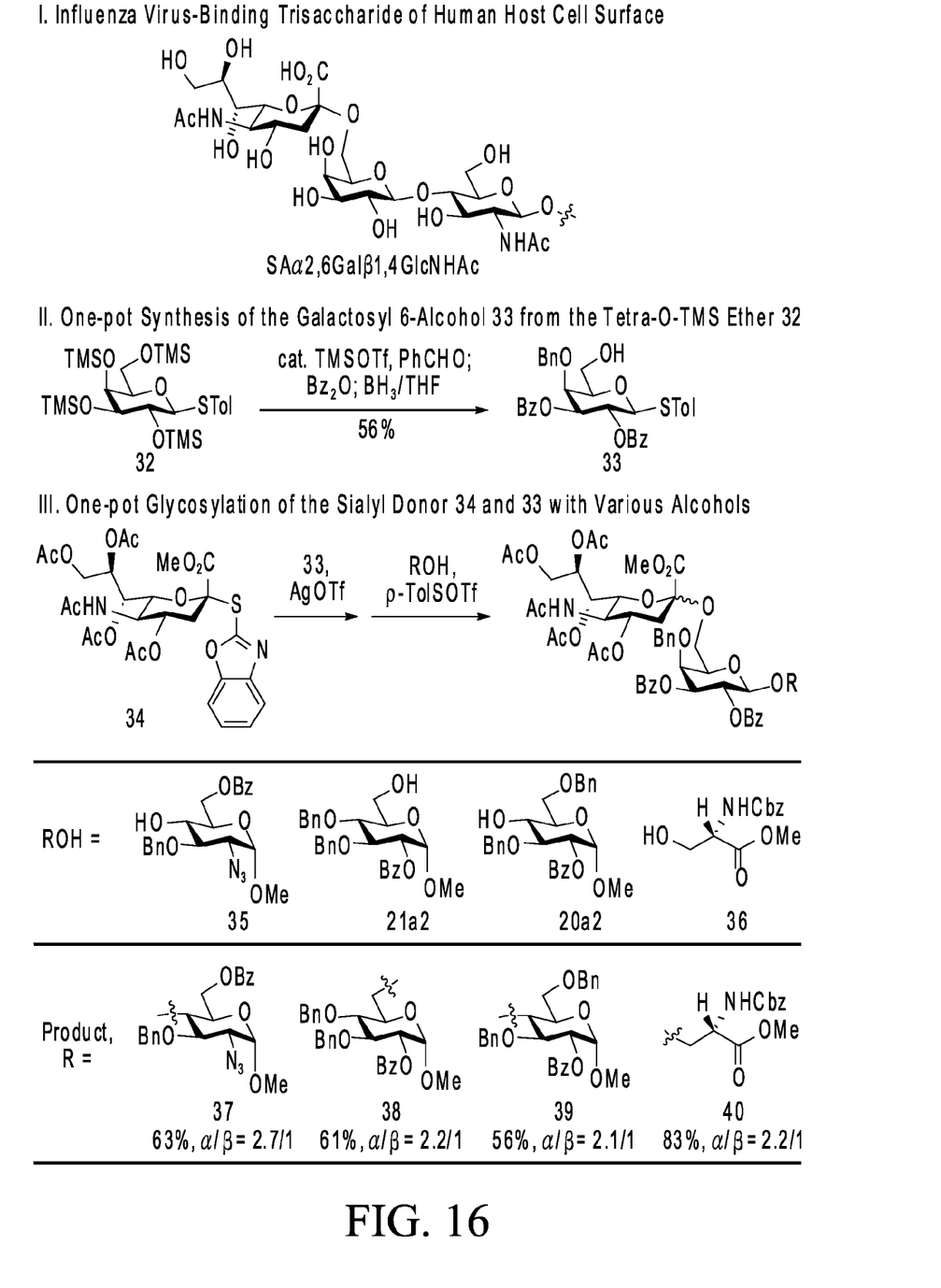
FIG. 16 illustrates the one-pot synthesis of influenza virus-binding trisaccharide library using the sialyl donor as the starting sugar unit according to the present invention.

FIG. 16 illustrates the one-pot synthesis of influenza virus-binding trisaccharide library using the sialyl donor as the starting sugar unit according to the present invention. The H5N1 avian influenza virus continues to sweep across the globe and becomes a horrible public threat around the world. Direct bird-to-human transmission is considered as a potential threat since the introduction of viral mutations can cause a switch in receptor specificity from D-sialic acids attached to D-galactose in □2,3-linkages (avian) to □2,6-linkages (human). A trisaccharide unit, SA□2,6Gal□1,4GlcNHAc, is identified as a host cell receptor for hemagglutinin binding during the initial step of viral infection. To tackle this problem, we present the one-pot synthesis of this trisaccharide and its derivatives. The D-galactopyranosyl 6-alcohol 33 was prepared from the tetra-O-TMS ether 32 in 56% yield via the one-pot protection strategy, involving 4,6-O-benzylidenation, 2,3-dibenzoylation, and O6-ring opening. All the initial attempts for the coupling of 33 with various sialyl donors bearing different anomeric leaving groups and protecting groups failed to yield the desired disaccharides, except the utilization of compound 34 in a mixed solvent of $CH_2Cl_2$ and $Et_2O$ that led to the α-isomer as the major product. AgOTf-activated assembly of 34 and 33 followed by PhSOTf-promoted coupling with the alcohols 35, 21a2, 20a2, and 36 in a one-pot manner afforded the expected trisaccharides 37, 38, and 39 as well as the glycoconjugate 40, respectively. These products and their β-sialyl isomers could be purified by column chromatography, individually, and the stereochemistry of each diastereoisomer was well-characterized through analysis of its $^1H$, $^{13}C$, DEPT, $^1H$—$^1H$ COSY, $^1H$—$^{13}C$ COSY, and NOESY NMR spectra.

In conclusion, the present invention provides an efficient method for regioselective, combinatorial, orthogonal, and one-pot protection of monosaccharides. Conceptually, this is the first approach to discriminate sugar polyols in a single flask, using a single catalyst. Via the TMSOTf-catalyzed reaction, the desired building block with differential protective group pattern can be accessed easily after a workup and single purification. The reaction conditions are optimized on D-glucopyranosides and should be applied to other sugars as well. This new protocol in conjunction with one-pot glycosylation greatly expedites the synthesis of oligosaccharides, as exemplified by a rapid preparation of β-1,6-glucans with various sugar units and influenza virus-binding trisaccharide library, thus may offer a simple, practical, and convenient tool to solve this long-standing problem in carbohydrate synthesis.

Example 1

General Procedure for the One-Pot Synthesis of 2-Alcohol Glucoses in Table 1

Referring to FIG. 7, to a solution of compound 16a or 16b (207 μmol), ArCHO (218 μmol), and freshly dried 3 Å molecular sieves (150 mg) in dichloromethane (1.5 mL) was added TMSOTf (31.7 μmol) at −86° C. under nitrogen atmosphere. The mixture was stirred at same temperature for 2 h, and $Et_3SiH$ (228 μmol), RCHO (248 μmol) and TMSOTf (15.9 μmol) were sequentially added to the reaction solution. After stirring for another 5 h, TBAF (0.41 mmol) was added to the mixture, the reaction flask was gradually warmed up to room temperature, and the solution was kept stirring overnight. The whole mixture was filtered through a pad of celite, and the filtrate was diluted with saturated $NaHCO_{3(aq.)}$(10 mL). The aqueous layer was extracted with EtOAc (3×10 mL), and the combined organic layers were washed with brine, dried over anhydrous $MgSO_4$, filtered, and concentrated in vacuo. The residue was purified by flash column chromatography on silica gel to provide the desired 2-alcohol glucoses.

Example 2

General Procedure for the One-Pot Synthesis of Fully Protected Monosaccharides in Table 2

Referring to FIG. 8, TMSOTf (31.7 μmol) was added to a mixture of compound 16a or 16b (207 μmol), ArCHO (218 μmol), and freshly dried 3 Å molecular sieves (150 mg) in dichloromethane (1.5 mL) at −86° C. under nitrogen atmosphere. After stirring at the same temperature for 2 h, $Et_3SiH$ (228 μmol), RCHO (248 μmol) and TMSOTf (15.9 μmol) were consecutively added to the solution, and the mixture was stirred for another 5 h. TBAF (0.41 mmol) was added to the solution, the reaction flask was gradually warmed up to room temperature, and the mixture was kept stirring overnight. For 2-O-esterification, $Et_3N$ (3.11 mmol) and acid anhydride (1.04 mmol) were sequentially added to the reaction mixture [For 2-O-etherification, anhydrous N,N-dimethylformamide (3 mL), alkylbromide (0.62 mmol), and NaH (0.62 mmol) were sequentially added to it at 0° C.], and the solution was stirred at room temperature for another 12 h. The whole mixture was filtered through a pad of celite, the filtrate was diluted with $H_2O$ (20 mL), and the aqueous layer was extracted with EtOAc (3×15 mL). The combined organic layers were washed with brine, dried over anhydrous $MgSO_4$, filtered, and concentrated in vacuo to give a residue, which was purified by flash column chromatography to provide the desired fully protected monosaccharides.

Example 3

General Procedure for the One-Pot Synthesis of 3-Alcohols in Supplementary Table 3

Referring to FIG. 9, a mixture of compound 16a or 16b (207 μmol), PhCHO (218 μmol), and freshly dried 3 Å molecular sieves (150 mg) in dichloromethane (1.5 mL) was stirred at −86° C. under nitrogen. TMSOTf (31.7 μmol) was added to the solution, and the mixture was kept stirring at the same temperature for 2 h. Et$_3$SiH (228 μmol), anisaldehyde (248 μmol) and TMSOTf (15.9 μmol) were consecutively added to the reaction solution, the mixture was stirred for another 5 h, TBAF (0.41 mmol) was added to the solution, and the reaction flask was gradually warmed up to room temperature overnight. For 2-O-esterification, Et$_3$N (3.11 mmol) and acid anhydride (1.04 mmol) were sequentially added to the reaction solution [For 2-O-etherification, anhydrous N,N-dimethylformamide (3 mL), alkylbromide (0.62 mmol), and NaH (0.62 mmol) were sequentially added to it at 0° C.], and the mixture was stirred at room temperature for another 12 h. H$_2$O (15 mL) was added to the solution, the whole mixture was vigorously stirred for 5 min, and the aqueous layer was removed from the reaction bottle by using a dropper. DDQ (621 μmol) was then added to the solution, and the mixture was stirred at room temperature for another 3 h. The reaction mixture was filtered through a pad of celite, and the filtrate was diluted with saturated NaHCO$_3$(aq.) (15 mL). The aqueous layer was extracted with EtOAc (3×10 mL), and the combined organic layers were washed with brine, dried over anhydrous MgSO$_4$, filtered, and concentrated in vacuo. Purification of this residue via flash column chromatography on silica gel furnished the desired 3-alcohol glucoses.

Example 4

General Procedure for the One-Pot Synthesis of Fully Protected Monosaccharides in Table 4

Figure 10:
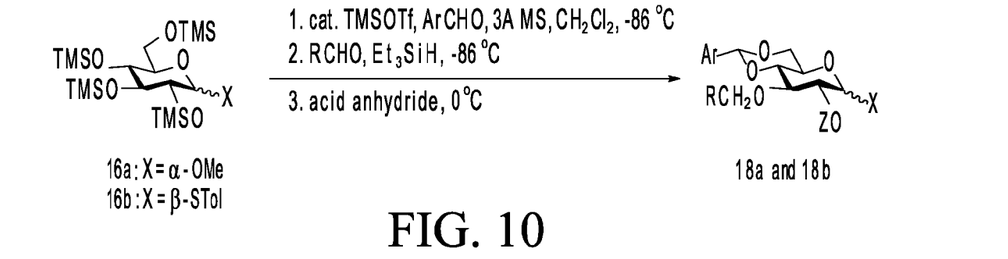
FIG. 10 illustrates the general procedure for the one-pot synthesis of fully protected monosaccharides in Table 4 according to one embodiment of the present invention.

Referring to FIG. 10, to a solution of compound 16a or 16b (207 μmol), ArCHO (218 μmol), and freshly dried 3 Å molecular sieves (150 mg) in dichloromethane (1.5 mL) was added TMSOTf (31.7 μmol) at −86° C. under nitrogen atmosphere. After stirring at the same temperature for 2 h, Et$_3$SiH (228 μmol), RCHO (248 μmol) and TMSOTf (15.9 μmol) were sequentially added to the solution, and the mixture was kept stirring for another 5 h. Acid anhydride (621 μmol) and TMSOTf (82.8 μmol) were consecutively added to the solution, the reaction flask was gradually warmed up to 0° C., and the mixture was stirred at the same temperature overnight. The whole solution was filtered through a pad of celite, and the filtrate was diluted with saturated NaHCO$_3$(aq.) (10 mL). The aqueous layer was extracted with EtOAc (3×10 mL), and the combined organic layers were washed with brine, dried over anhydrous MgSO$_4$, filtered, and concentrated in vacuo. The residue was purified by flash column chromatography to yield the expected fully protected monosaccharides.

Example 5

General Procedure for the One-Pot Synthesis of 3-Alcohols in Table 5

Figure 11:
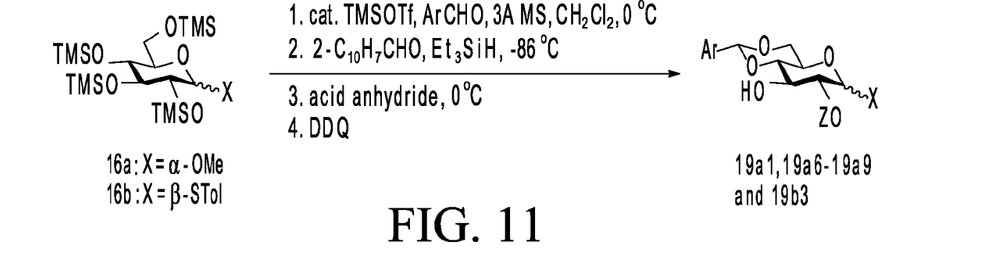
FIG. 11 illustrates the general procedure for the one-pot synthesis of 3-alcohols in Table 5 according to one embodiment of the present invention.

Referring to FIG. 11, TMSOTf (31.7 μmol) was added to a mixture of compound 16a or 16b (207 μmol), ArCHO (218 μmol), and freshly dried 3 Å molecular sieves (150 mg) in dichloromethane (1.5 mL) at −86° C. under nitrogen atmosphere. After 2 h, Et$_3$SiH (228 μmol), 2-naphthaldehyde (248 μmol) and TMSOTf (15.9 μmol) were successively added to the solution, and the mixture was kept stirring for another 5 h. Acid anhydride (621 μmol) and TMSOTf (82.8 μmol) were consecutively added to the solution, the reaction flask was gradually warmed up to 0° C., and the mixture was stirred at the same temperature overnight. DDQ (621 μmol) was then added to the reaction solution, and the mixture was kept stirring for 5 h. The whole mixture was filtered through a pad of celite, the filtrate was diluted with saturated NaHCO$_{3(aq.)}$ (10 mL), and the aqueous layer was extracted with EtOAc (3×10 mL). The combined organic layers were washed with brine, dried over anhydrous MgSO$_4$, filtered, and concentrated in vacuo to provide a residue, which was purified by flash column chromatography to afford the 3-alcohol glucoses.

Example 6

General Procedure for the One-Pot Synthesis of 4-Alcohols in Table 6

Figure 12:
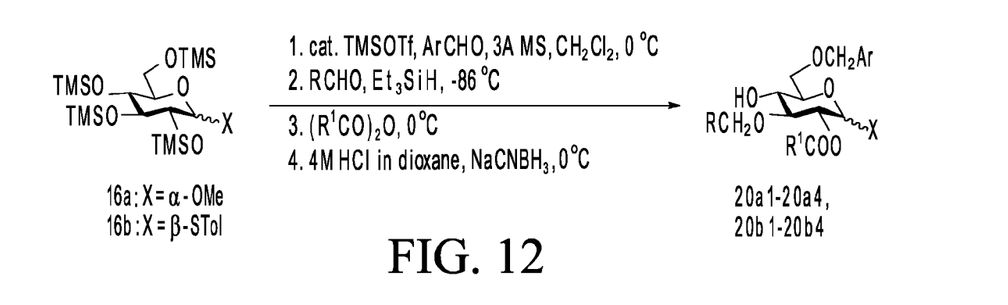
FIG. 12 illustrates the general procedure for the one-pot synthesis of 4-alcohols in Table 6 according to one embodiment of the present invention.

Referring to FIG. 12, a mixture of compound 16a or 16b (207 μmol), PhCHO (218 μmol), and freshly dried 3 Å molecular sieves (150 mg) in dichloromethane (1.5 mL) was stirred at −86° C. under nitrogen. TMSOTf (31.7 μmol) was added to the solution, and the mixture was kept stirring at the same temperature for 2 h. Et$_3$SiH (228 μmol), RCHO (248 μmol) and TMSOTf (15.9 μmol) were sequentially added to the reaction solution, the mixture was stirred for another 5 h, and acid anhydride (621 μmol) and TMSOTf (82.8 μmol) were successively added to the solution. The reaction flask was gradually warmed up to 0° C., and the mixture was stirred at the same temperature overnight. NaCNBH$_3$ (3.11 mmol) was then added to the reaction solution, and the pH number of the solution was controlled at 1~2 via the addition of 4M HCl in 1,4-dioxane at 0° C. The reaction flask was gradually warmed up to room temperature, and the mixture was kept stirring for another 1 h. The reaction mixture was filtered through a pad of celite, and the filtrate was carefully neutralized by saturated NaHCO$_{3(aq.)}$ (20 mL). The aqueous layer was extracted with EtOAc (3×10 mL), and the combined organic layers were washed with brine, dried over anhydrous MgSO$_4$, filtered, and concentrated in vacuo. Purification of this residue through flash column chromatography on silica gel led to the desired 4-alcohol glucoses.

Example 7

General Procedure for the One-Pot Synthesis of 6-Alcohols in Table 7

Figure 13:
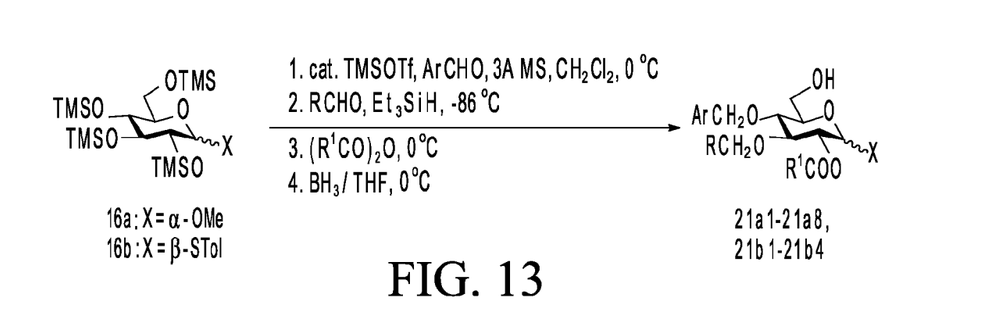
FIG. 13 illustrates the general procedure for the one-pot synthesis of 6-alcohols in Table 7 according to one embodiment of the present invention.

Referring to FIG. 13, to a solution of compound 16a or 16b (207 μmol), ArCHO (218 μmol), and freshly dried 3 Å molecular sieves (150 mg) in dichloromethane (1.5 mL) was added TMSOTf (31.7 μmol) at −86° C. under nitrogen atmosphere. After stirring at the same temperature for 2 h, Et$_3$SiH (228 μmol), RCHO (248 μmol) and TMSOTf (15.9 μmol) were sequentially added to the solution, and the mixture was kept stirring for another 5 h. Acid anhydride (621 μmol) and TMSOTf (82.8 μmol) were consecutively added to the solution, the reaction flask was gradually warmed up to 0° C., and the mixture was stirred at the same temperature overnight. 1M solution of borane in THF (1.04 mmol) was added to the reaction mixture followed by addition of TMSOTf (0.10 mmol), and the solution was kept stirring for another 6 h. The reaction was slowly quenched by MeOH (10 mL) at 0° C., the mixture was filtered through a pad of celite, and the filtrate was coevaporated with MeOH in vacuo. The residue was dissolved in EtOAc (10 mL), water (10 mL) was added to the mixture, and the aqueous layer was extracted with EtOAc (3×10 mL). The combined organic layers were washed with brine, dried over anhydrous MgSO$_4$, filtered, concentrated in vacuo, and purified by flash column chromatography to give the desired 6-alcohol glucoses.

The above-described embodiments of the present invention are intended to be illustrative only. Numerous alternative embodiments may be devised by those skilled in the art without departing from the scope of the following claims.

What is claimed is:

1. A method for preparing hexose derivatives, comprising the steps of:
   providing a silylated hexose;
   treating the silylated hexose with a first carbonyl compound having a carbonyl group in the presence of a catalyst to form a ketalized hexose;
   converting the ketalized hexose into an etherized hexose having an ether group by treating the ketalized hexose with a second carbonyl compound having a carbonyl group followed by treating with a first reductant to convert the carbonyl group of the second carbonyl compound into the ether group by a reduction reaction in an acidic condition; and
   converting the etherized hexose into a target hexose derivative having a hydroxyl group.

2. The method for preparing hexose derivatives of claim 1, wherein the silylated hexose is a per-silylated hexose.

3. The method for preparing hexose derivatives of claim 1, wherein the silylated hexose is a per-trimethylsilylated hexose, a per-triethylsilylated hexose or a per-dimethylethylsilylated hexose.

4. The method for preparing hexose derivatives of claim 1, wherein the first carbonyl compound is different from the second carbonyl compound.

5. The method for preparing hexose derivatives of claim 1, wherein the first carbonyl compound is the same as the second carbonyl compound.

6. The method for preparing hexose derivatives of claim 1, wherein the catalyst is trimethylsilyl trifluoromethanesulfonate or metal trifluoromethanesulfonate.

7. The method for preparing hexose derivatives of claim 6, wherein the metal trifluoromethanesulfonate is selected from the group consisting of copper(II) trifluoromethanesulfonate [$Cu(OTf)_2$], oxavanadium(IV) trifluoromethanesulfonate [$V(O)(OTf)_2$], Bismuth(III) trifluoromethanesulfonate [$Bi(OTf)_3$], Hafnium(IV) trifluoromethanesulfonate [$Hf(OTf)_4$], Samarium(III) trifluoromethanesulfonate [$Sm(OTf)_3$], Scandium(III) trifluoromethanesulfonate [$Sc(OTf)_3$], Praseodymium(III) trifluoromethanesulfonate [$Pr(OTf)_3$], Neodymium trifluoromethanesulfonate [$Nd(OTf)_3$], Ytterbium trifluoromethanesulfonate [$Yb(OTf)_3$], Europium(III) trifluoromethanesulfonate [$Eu(OTf)_3$], Gadolinium(III) trifluoromethanesulfonate [$Gd(OTf)_3$].

8. The method for preparing hexose derivatives of claim 1, wherein the ketalized hexose has an arylidene acetal group.

9. The method for preparing hexose derivatives of claim 1, wherein the first reductant is triethylsilane or dimethylethyl silane.

10. The method for preparing hexose derivatives of claim 1, wherein the step of converting the etherized hexose into a target hexose derivative is treating the etherized hexose with silylate-removing reagent to form a 2-alcohol hexose.

11. The method for preparing hexose derivatives of claim 10, wherein the silylate-removing reagent is tetrabutylammonium fluoride.

12. The method for preparing hexose derivatives of claim 10, further comprising a step of treating the 2-alcohol hexose with an electrophile under basic conditions to form a fully protected glycoside.

13. The method for preparing hexose derivatives of claim 12, further comprising a step of treating the fully protected glycoside with an oxidant to form a 3-alcohol hexose.

14. The method for preparing hexose derivatives of claim 13, wherein the oxidant is 2,3-Dichloro-5,6-dicyano-p-benzoquinone.

15. The method for preparing hexose derivatives of claim 1, wherein the step of converting the etherized hexose into a target hexose derivative is treating the etherized hexose with an anhydride followed by treating with an acid and a second reductant to form a 4-alcohol hexose.

16. The method for preparing hexose derivatives of claim 15, wherein the acid is hydrochloric acid and the second reductant is sodium cyanoborohydride.

17. The method for preparing hexose derivatives of claim 1, wherein the step of converting the etherized hexose into a target hexose derivative is treating the etherized hexose with an anhydride followed by treating with a second reductant and a lewis acid to form a 6-alcohol hexose.

18. The method for preparing hexose derivatives of claim 17, wherein the second reductant is borane and the lewis acid is trimethylsilyl trifluoromethanesulfonate.

19. The method for preparing hexose derivatives of claim 1, wherein the step of converting the etherized hexose into a target hexose derivative is treating the etherized hexose with an anhydride to form a fully protected glycoside.

20. The method for preparing hexose derivatives of claim 19, further comprising a step of treating the fully protected glycoside with an oxidant.

21. The method for preparing hexose derivatives of claim 20, wherein the oxidant is 2,3-Dichloro-5,6-dicyano-p-benzoquinone.

22. The method for preparing hexose derivatives of claim 1, wherein the hexose is D-glucose, D-talose, D-galactose, D-idose, D-gulose, D-mannose, D-altrose or D-allose.

23. The method for preparing hexose derivatives of claim 1, wherein the silylated hexose includes a functional group selected from the group consisting of α-OR, β-OR, α-SR, β-SR, α-SeR, β-SeR, α-F and β-F.

24. The method for preparing hexose derivatives of claim 1, wherein the first carbonyl compound is selected from the group consisting of aldehyde and ketone.

25. The method for preparing hexose derivatives of claim 1, wherein the second carbonyl compound is selected from the group consisting of aldehyde and ketone.

* * * * *